United States Patent [19]
White

[11] Patent Number: 5,728,510
[45] Date of Patent: Mar. 17, 1998

[54] PROSTHETIC ARTICLES AND METHODS FOR PRODUCING SAME

[75] Inventor: Eugene W. White, Rossiter, Pa.

[73] Assignee: Interpore International, Irvine, Calif.

[21] Appl. No.: 542,846

[22] Filed: Oct. 13, 1995

Related U.S. Application Data

[63] Continuation of Ser. No. 308,762, Sep. 19, 1994, Pat. No. 5,487,933, which is a continuation-in-part of Ser. No. 134,260, Oct. 8, 1993, Pat. No. 4,455,100, which is a division of Ser. No. 647,999, Jan. 30, 1991, Pat. No. 5,348,788.

[51] Int. Cl.$^6$ ........................................ G03C 5/00
[52] U.S. Cl. ................ 430/323; 430/320; 430/326; 264/161; 264/219; 219/69.17; 216/56; 216/100
[58] Field of Search ................ 430/269, 320, 430/323, 326; 264/161, 219; 216/56, 100; 219/69.17

[56] References Cited

U.S. PATENT DOCUMENTS

| | | | |
|---|---|---|---|
| 3,126,978 | 3/1964 | Bergstrom | 181/290 |
| 3,852,045 | 12/1974 | Wheeler et al. | 29/182 |
| 3,852,832 | 12/1974 | McGhan et al. | 3/36 |
| 3,929,921 | 12/1975 | Wilke et al. | 260/666 A |
| 4,231,979 | 11/1980 | White et al. | 264/81 |
| 4,439,391 | 3/1984 | Hung | 264/317 |
| 4,673,409 | 6/1987 | Van Kampen | 623/23 |
| 4,722,870 | 2/1988 | White | 428/621 |
| 4,839,215 | 6/1989 | Starling et al. | 428/131 |
| 4,861,733 | 8/1989 | White | 501/1 |
| 4,865,603 | 9/1989 | Noiles | 623/18 |
| 4,976,736 | 12/1990 | White et al. | 623/16 |
| 4,978,355 | 12/1990 | Frey et al. | 623/16 |
| 5,011,494 | 4/1991 | von Recum et al. | 623/11 |
| 5,030,233 | 7/1991 | Ducheyne | 623/16 |
| 5,053,264 | 10/1991 | Beretta | 428/131 |
| 5,147,402 | 9/1992 | Bohler et al. | 623/16 |
| 5,192,324 | 3/1993 | Kenna | 623/16 |
| 5,222,987 | 6/1993 | Jones | 623/66 |
| 5,282,861 | 2/1994 | Kaplan | 623/16 |
| 5,342,919 | 8/1994 | Dickens, Jr. et al. | 528/23 |
| 5,455,100 | 10/1995 | White | 428/131 |

*Primary Examiner*—George F. Lesmes
*Assistant Examiner*—Bernard P. Codd
*Attorney, Agent, or Firm*—Hopgood, Calimafde, Kalil & Judlowe, LLP

[57] ABSTRACT

A porous mesh structure is prepared in sheet form having a unique arrangement of main and secondary troughs on a first surface, and openings extending therethrough. The arrangement of troughs and openings creates an elaborate matrix of pores when the sheet is layer on itself in a front to back manner. This arrangement of pores and support structure emulates certain cortical bone structures and is therefore very effective as an artificial bone material. In addition, the porous structure has significant other potential uses outside the medical field and can be effectively applied accordingly, based on its fundamental, structural attributes.

4 Claims, 5 Drawing Sheets

PROSTHETIC ARTICLES AND METHODS FOR PRODUCING SAME

RELATED APPLICATIONS

This is a continuation of application Ser. No. 308,762 filed Sep. 19, 1994, now U.S. Pat. No. 5,487,933, which is a continuation-in-part of application Ser. No. 134,260 filed Oct. 8, 1993, now U.S. Pat. No. 5,455,100, which is a divisional of application Ser. No. 647,999 filed Jan. 30, 1991, now U.S. Pat. No. 5,348,788.

FIELD OF THE INVENTION

The present invention generally relates to materials which simulate human tissue for use as prosthesis. More particularly, the invention is directed to novel three-dimensional structures made from select materials and processes for producing the three-dimensional structures from the select materials.

BACKGROUND OF THE INVENTION

Prosthetic materials are engineered elements which can achieve biological function when placed within a living organism. An important class of prosthetic materials are those which are used to repair and replace human body tissue such as osseous matter. To replace biological tissue in an acceptable, long lasting manner, the replacement materials must join with the surrounding living matter. Proper melding is achieved through the use of an appropriate material having a micro-network of capillaries permeating the structure to permit living tissue in-growth.

Such porous networks must be continuous, permitting unrestricted passage of blood and other body fluids from the surrounding tissue while also providing structural support. This can be easily envisioned in the design of artificial bone wherein osseous replacement materials must support the forces and stresses associated with the skeletal system and simultaneously allow passage of blood gases, nutrients, waste products and other extracellular material to and from the surrounding tissue.

In reconstructive surgery such as repair of highly comminuted fractures, healing can be accelerated by inclusion of materials having such porous matrix adjacent the break point to enhance bone growth. Rebuilding of damaged long bones can also benefit from insertion of such porous prosthetic materials to re-achieve the desired pre-damage shape and strength.

Such porous yet semi-rigid materials are found in nature. For example, spiny starfish, certain sea urchins and coral exhibit a solid structure formed of calcium carbonate having a network of interconnecting pores and significant void volume in the form of a micro-porous matrix. Specifically, the slate pencil sea urchin has cigar-shaped protrusions that have a void volume of 50 percent and a porous structure with pore diameters of approximately 25 μm. Certain coral provide similar attributes with pore diameters of approximately 250–600 μm.

In the past, these aquatic materials were used to form biologically acceptable structures such as through hydrothermal treatment of the calcium carbonate skeletons to form hydroxyapatite. More detailed discussion of such techniques may be found in U.S. Pat. Nos. 3,890,107, 3,929,971, 4,231,979, 4,722,870 and 4,861,733, the teachings of which are incorporated by reference herein.

Although these procedures offer a unique class of structures, they are accompanied by several significant drawbacks. The naturally forming aquatic structures are never completely uniform and often exhibit imperfections detrimental to surgical implantation. In addition, the materials are expensive to harvest, and such gleaning of nature has raised environmental impact concerns in some quarters.

These problems have led to a search for techniques to engineer and manufacture porous materials having specifically delineated structural properties in a controlled manner. In this search, applicant has developed a unique collection of porous articles of the type discussed above. These are disclosed in U.S. Pat. No. 5,348,788, the contents of which is incorporated by reference herein as if restated in full.

Related thereto, applicant has developed several important advancements which are described herein below.

OBJECTS AND SUMMARY OF THE PRESENT INVENTION

It is an object of the present invention to provide materials which simulate human tissue for use in repair and replacement of osseous matter in the form of porous materials that have a three-dimensional network of interconnecting pores.

Another object of the present invention is to provide materials which simulate human osseous tissue for use as prosthesis in the form of porous materials that have a three-dimensional network of interconnecting pores and a void volume percent between 20 and 80.

It is another object of the present invention to provide a porous article with a substantially anisotropic distribution of pores wherein the pore diameter ranges between 25 and 2500 μm.

It is a further object of the present invention to provide biologically compatible, curable, bone-like compositions and three-dimensional structures made therefrom.

It is yet another object of the invention to provide biologically compatible hydroxyapatite, hydroxyapatite/collagen and hydroxyapatite/gelatin compositions and three-dimensional structures made therefrom.

It is a further object of the present invention to provide a bone substitute material which when properly configured simulates osteon evacuated cortical bone.

It is another object of the present invention to provide a method for manufacturing biologically compatible, curable, bone-like compositions and three-dimensional structures made from such compositions for use as cement in bone repair or as bone-substitute materials.

It is also another object of the invention to provide a method for making hydroxyapatite compositions, hydroxyapatite/collagen and hydroxyapatite/gelatin compositions and three-dimensional structures made from such compositions for use as cement in bone repair or as bone-substitute materials as tailored to specific system constraints.

It is yet another object of the present invention to provide methods for making porous structures that have varying industrial applications such as heat exchangers, spargers, catalytic support matrices and filter media.

The above and other objects of the present invention are realized in illustrative compositions suitable for use in repair of damaged bone and bone-simulating material comprising biologically compatible, curable, bone-like compositions such as hydroxyapatite, hydroxyapatite/collagen, hydroxyapatite/gelatin, and other bio-materials such as polyfunctional carboxylic acid substrates described in U.S. Pat. No. 4,218,255, calcium phosphate slurries and pastes described in U.S. Pat. No. 4,612,053, non-bioresorbable calcium phosphate described in U.S. Pat. No. 4,619,655, polymer based calcium phosphates described in U.S. Pat. No. 4,843,112, carbonated hydroxyapatite such as described in U.S. Pat. No. 4,880,610, organic acid-calcium phosphates described in U.S. Pat. No. 4,902,649, acidic phosphates described in U.S. Pat. No. 5,053,212, acidic citrates described in U.S. Pat. No. 5,149,368, polysaccharide calcium phosphates described in U.S. Pat. No. 5,180,426, calcium alkali-polyfunctional carboxylic acid substrates described in U.S. Pat. No. 5,218,035, calcium alkali-acidic citrates described in U.S. Pat. No. 5,262,166, calcium salts-polyfunctional acid substrates described in U.S. Pat. No. 5,281,265, and tannin/collagen-calcium phosphates described in WIPO Patent Publication Nos. WO 90/00892 and WO 90/01341, the teachings of which are herein incorporated by reference.

A discussion of some of these materials may also be found in Stupp et al., *Organoapatites: Materials for Artificial Bone*, J. Biomedical Materials Res., Vol. 27, pages 301–311 (1993), the teachings of which is incorporated by reference herein.

Hydroxyapatite has a nominal composition of $Ca_{10}(PO_4)_6(OH)_2$ and comprises the principal mineral in human bones. The metal mold used in the forming process is machined by various surface shaping techniques that are known, such as computer guided milling, photolithography and electron discharge machining. Suitable mold metals include steel and brass and other rigid substrate materials well known to those skilled in the art.

A porous mesh suitable for emulating cortical bone structure can be made as follows. The mesh attributes are first formed in a master that is machined from metal sheets in a predetermined, scaled pattern on a specifically delineated surface area. From the metal masters are produced, by replication, as many "negative working masters" as desired.

The negative masters are made of silicone rubber or other suitable substitute materials evident to one skilled in these arts. With a light coating of mold release agent, whole sheets of replicas are retrieved. Silicone rubber is ideal for some applications but other applications may require more rigid materials. The silicone negative master is the inverted replica of the original metal master.

Bone substitute materials are subsequently produced from the silicone negative masters. Preferably, a mixture containing specific and predetermined amounts of water, gelatin and calcium phosphate are prepared at a set temperature. Bovine gelatin $(C_{76}H_{124}O_{29}N_{24}S_x)$ can be used but any albumin usually obtained from boiling animal bones and cartilage under pressure with water are suitable. Collagen may also be added as an alternate or additional reagent. Collagen of the type contemplated herein includes a hydroxyproline, glycine-type protein which is the chief organic constituent of connective tissue and bones, which yields gelatin when steam autoclaved in water, and which is usually comprised of 50.75% carbon, 6.47% hydrogen and 17.86% nitrogen.

The preferred mixture is applied hot with a suitable spatula to a selected silicone negative master and worked into the formed pattern. The assembly is then chilled for a predetermined time period allowing the gelatin to set. The gelled mix is released from the master and wrapped on a suitably shaped mandril. The shape of the selected mandril closely corresponds to the shape of the actual bone in the desired repair site. After the suitable shape is achieved, the hydroxyapatite material is slipped off the mandril and allowed to dry.

The resulting shaped material must then be stabilized before use in the human body. Hydroxyapatite can be stabilized by known techniques such as thermal/vacuum processing or chemical cross-linking. Gelatin cross-link treatment renders the gelatin within the hydroxyapatite/gelatin composite less biodegradable. Alternatively, the final process stage can be a high temperature burn off of the gelatin binder to sinter the hydroxyapatite body for strength. If such a burn off is contemplated, the starting materials should have a higher loading of calcium phosphate relative to the gelatin.

The foregoing features of the present invention may be more fully appreciated by reference to the following detailed description of the specific embodiments thereof, in conjunction with the associated figures.

DETAILED DESCRIPTION OF THE PRESENT INVENTION

The present invention is directed to the preparation of a new man made structure comprised of materials suitable for use in repair of damaged bone and bone-simulating material comprising biologically compatible, curable, bone-like compositions such as hydroxyapatite, hydroxyapatite/collagen, hydroxyapatite/gelatin, and other bio-materials such as described in the above-noted patents.

The new sheet structure is specifically designed for assembly into a variety of shapes, not just rectangular blocks, that more closely correspond to the shapes of the actual bone in many repair sites such as hollow cylindrical or doubly curved plate shapes. The porous mesh sheets provide the basis for a three-dimensional structure that closely emulates the anisotropic network associated with cortical bone mass.

The generalized approach is to form a non-woven mesh in sheet stock form. This mesh has a uniform pattern of openings across its surface that extend through the sheet. In addition, this mesh has a uniform pattern of protrusions extending outward from the sheet's surface to a substantially constant height. These protrusions are distributed in a pattern that corresponds to the pattern associated with the openings, but offset therefrom, so that an even distribution of openings and protrusions across the mesh surface is established. The material used in forming this mesh and the amount of openings therein will define the mesh's flexibility.

The flexibility of the mesh is set according to the desired end use of the article.

The porous article is created by stacking the mesh in layers, wherein the sequence of the layers is alternated so that adjacent sheets are in contact by their respective protrusions or are back-to-back. When stacked in this manner, the resulting porous structure is a three-dimensional network of interconnecting pores.

Figure 1:
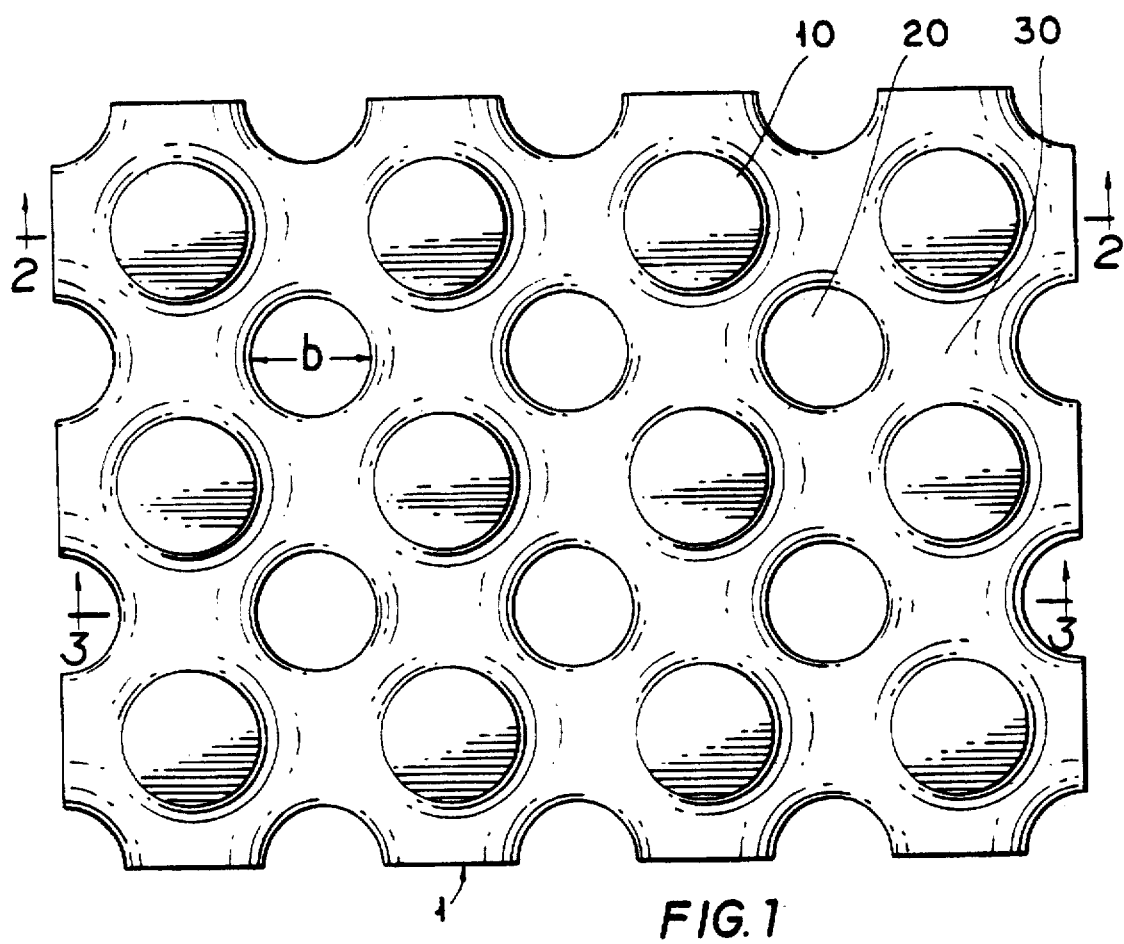
FIG. 1 shows a top plan view of one of the mesh structures prepared in accordance with the present invention.

Referring now to FIG. 1, an example of the above-noted mesh is presented. In this example, the protrusions 10 of mesh 1 have circular cross sections with a decreasing diameter that terminates with a plateau 40 of diameter "X". As can be seen, these protrusions are distributed across a substantial portion of mesh 1 in a substantially uniform coordinate grid pattern. Although a protrusion with a circular cross section is presented, other shapes may be used each having an effective diameter corresponding with that expressed in FIG. 1. In this context, the effective diameter reflects an associated structural interference preventing insertion into a corresponding opening in mesh 1.

Continuing in FIG. 1, a series of openings 20 are shown as distributed across the surface of mesh 1, in a pattern corresponding to that of the protrusions 10 but offset therefrom so that, as depicted, each opening 20 is at the center point of a rectangle defined by the four protrusions adjacent to that opening. The topographic surface resulting from this arrangement of openings and protrusions is further characterized by a series of troughs 30 extending between each pair of adjacent openings.

Figure 2:
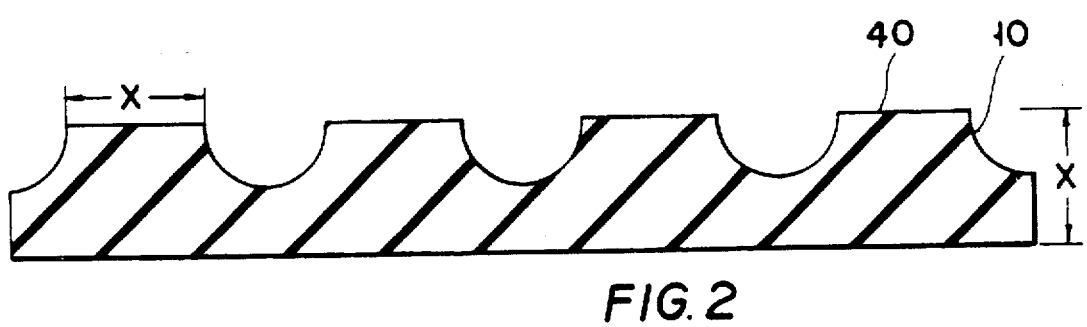
FIG. 2 is a cross-sectional view taken from line 2—2 in FIG. 1.

Turning now to FIG. 2, a cross section of mesh 1 is presented as taken from line 2—2 in FIG. 1. As indicated in this cross-section, the thickness of the mesh at trough 30 is one-half the maximum thickness of the mesh defined by the peak of protrusion 10. In addition, the circular plateau 40 of each protrusion has a diameter equal to "X". A second cross section, taken through line 3—3 of FIG. 1, is presented in FIG. 3. In this cross section, the openings are circular and have a diameter equal to "Y". The trough between adjacent protrusions is represented by semi-circle 32 which has an effective radius of Y/2. In the preferred embodiment, the diameter of the protrusion "X" is greater than the diameter of the opening "Y".

Figure 3:
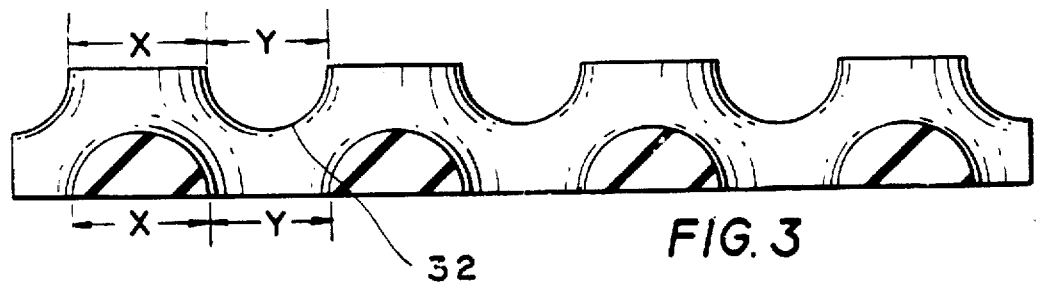
FIG. 3 is a cross-sectional view taken from line 3—3 in FIG. 1.
Figure 4:
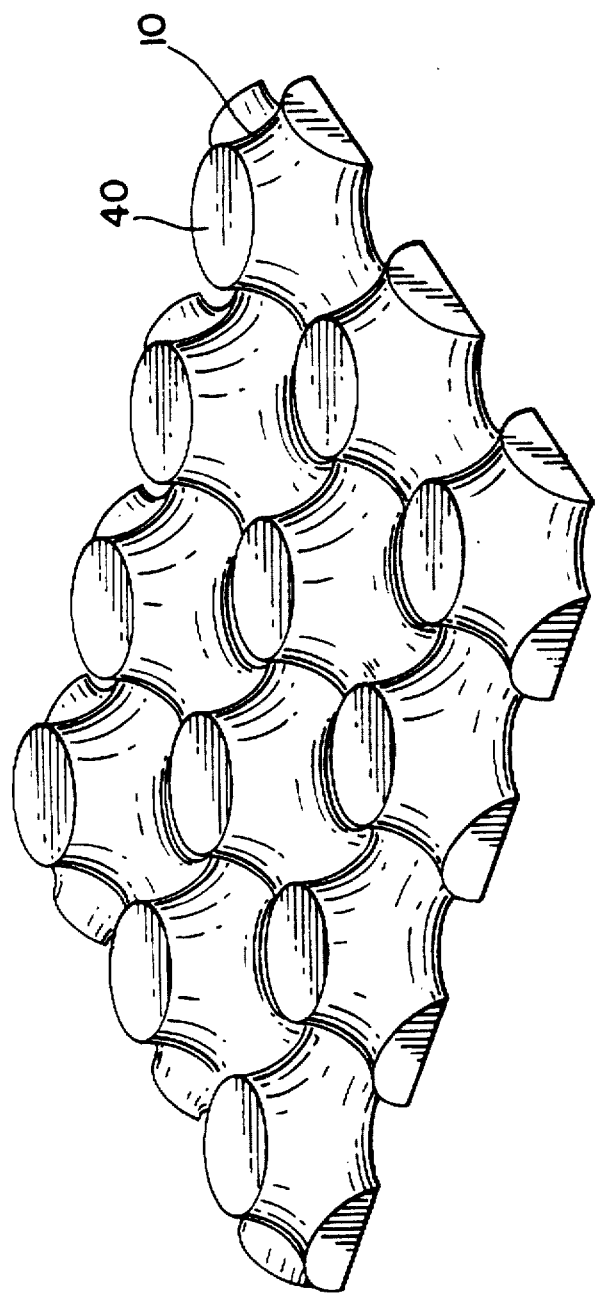
FIG. 4 depicts a perspective view of the mesh shown in FIG. 1.

In FIG. 4, a perspective representation of the mesh structure corresponding to FIGS. 1 through 3 is presented. This particular representation reflects the topographical properties of the mesh surface as a series of integrated protrusions 10 and openings 20 positioned according to a uniform pattern. In this particular embodiment, the mesh surface is an idealized minimal surface area connecting the plateaus for each protrusion 10 with the edge of openings 20 (hidden from view in FIG. 4). This minimal surface area defines the saddle-shaped troughs 30 between each adjacent pair of openings 20.

Figure 5:
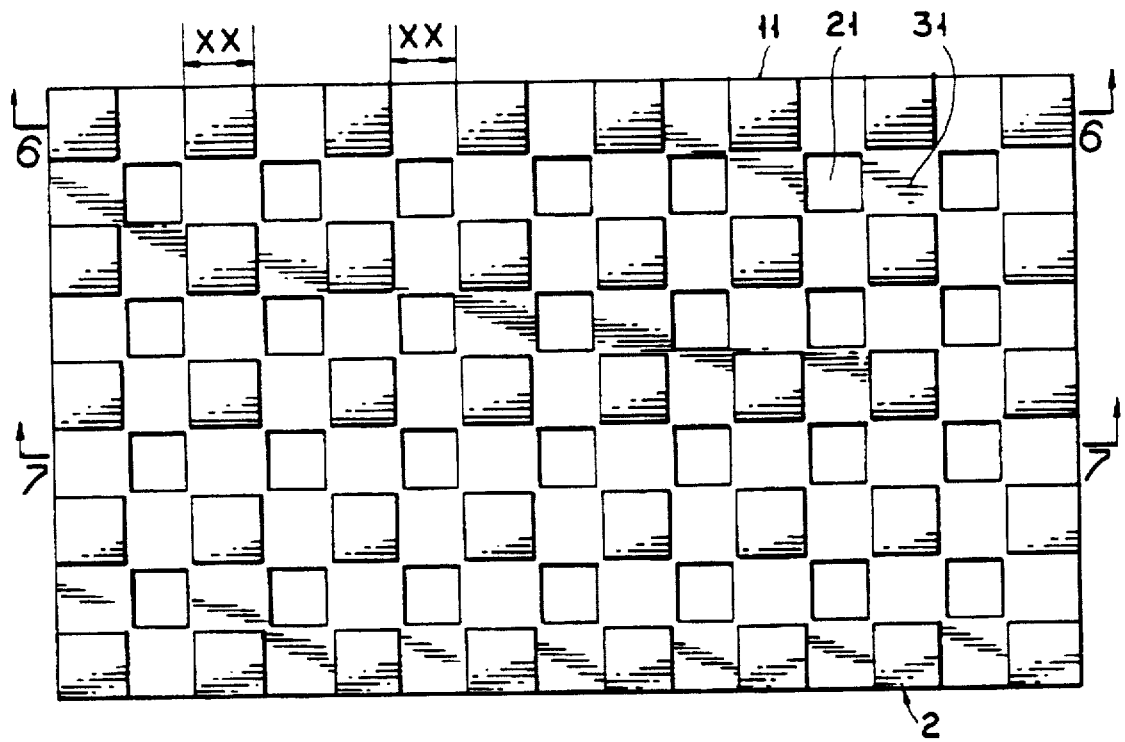
FIG. 5 provides a top plan view of a second mesh structure prepared in accordance with the present invention.

Turning now to FIG. 5, a further example of the inventive mesh is presented. In this figure, the protrusions 11, openings 21 and troughs 31 are square in shape. These elements are arranged in a three-element checkerboard pattern across the surface of mesh 2, wherein adjacent openings are separated by troughs as are adjacent protrusions.

Figure 6:
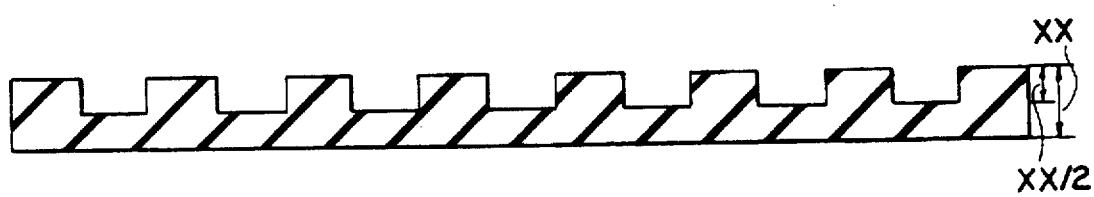
FIG. 6 is a cross-sectional view taken from line 6—6 in FIG. 5.
Figure 7:
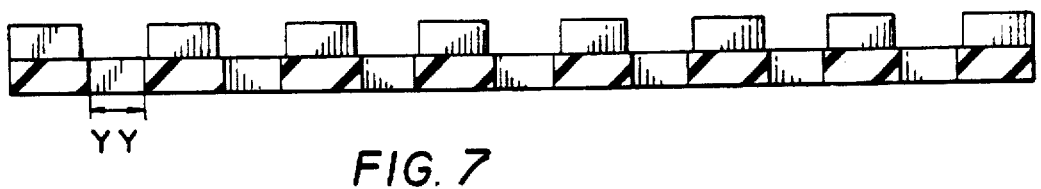
FIG. 7 is a cross-sectional view taken from line 7—7 in FIG. 5.

FIG. 6, a cross section of the mesh in FIG. 5 taken at line 6—6, provides the relative dimensions for the protrusions 11 and troughs 31. In this arrangement, the maximum mesh thickness at protrusion 11 is "XX" and the trough thickness is "XX/2". A second cross section taken at line 7—7 in FIG. 5 is presented in FIG. 7 indicating the relative size of openings 21 and troughs between the openings. In this arrangement, the opening width is "YY", wherein XX>YY.

Figure 8:
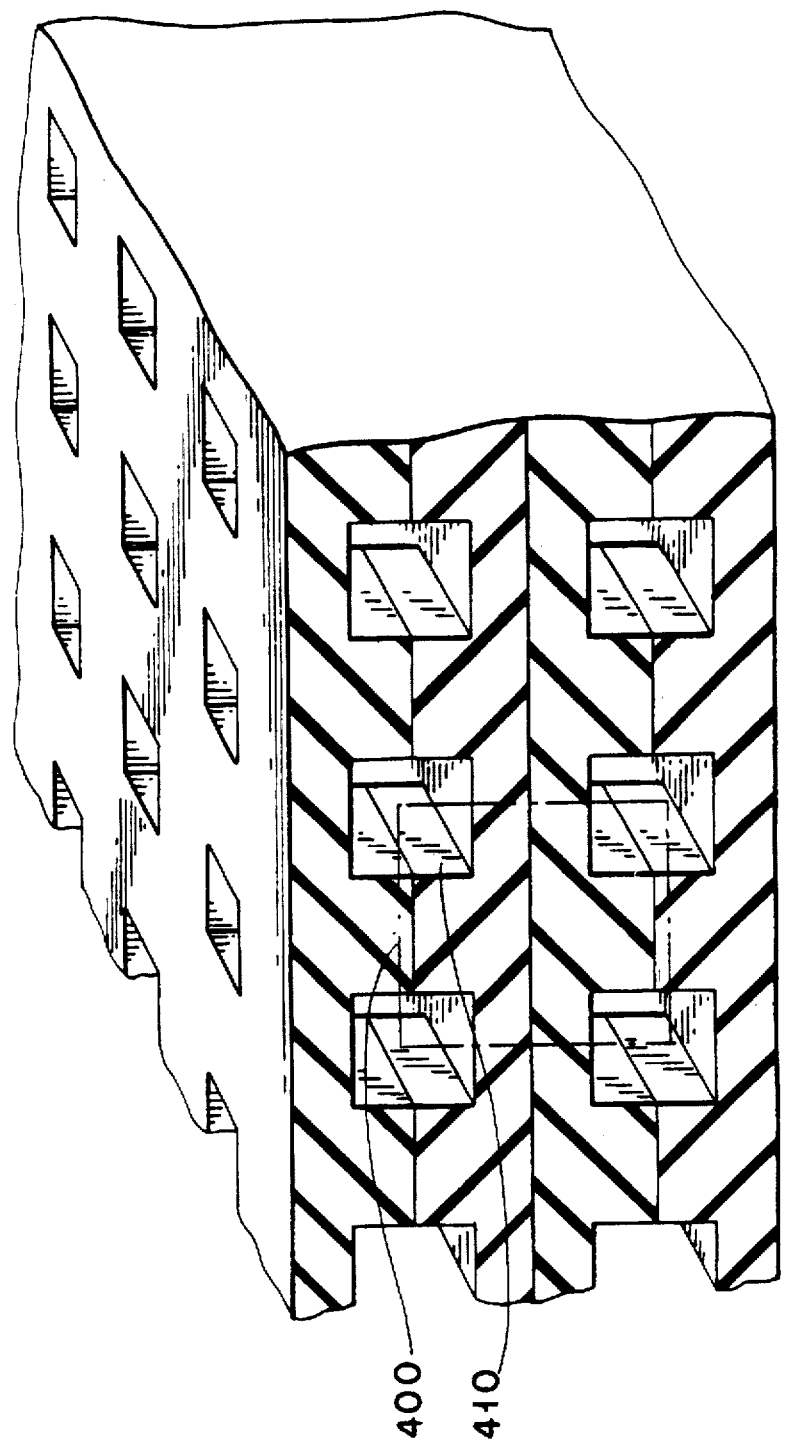
FIG. 8 provides a cross-sectional view taken through a row of protrusions for a series of alternating layers of the mesh shown in FIG. 5.

In FIG. 8, the cross section depicted in FIG. 6 is represented as layered on a mirrored image of itself. This represents the procedure for layering the mesh to build up the porous article forming a three-dimensional network of interconnecting pores. This is accomplished by taking the back-to-back mesh layers and further layering them to form a stack, wherein protrusions from one layer contact the protrusions extending from the adjacent layer. In this representation, a unit block 400 is defined as the repeating unit in the solid matrix of the porous article. More particularly, unit block 400 is interconnected to six adjacent blocks along the three orthogonal axes and by the protrusions 410, wherein two protrusions extend outward along each of the three orthogonal axes.

Figure 9A:
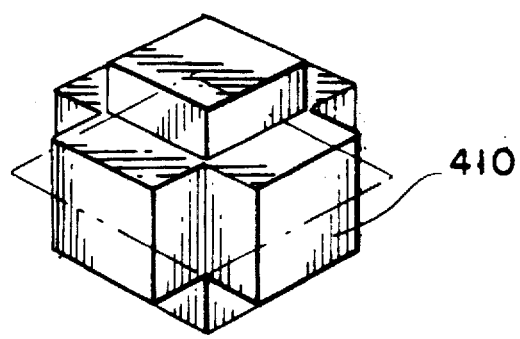
FIGS. 9A–9C provide perspective views of sample blocks used as the repeating units in the matrix in accordance with the present invention.
Figure 9B:
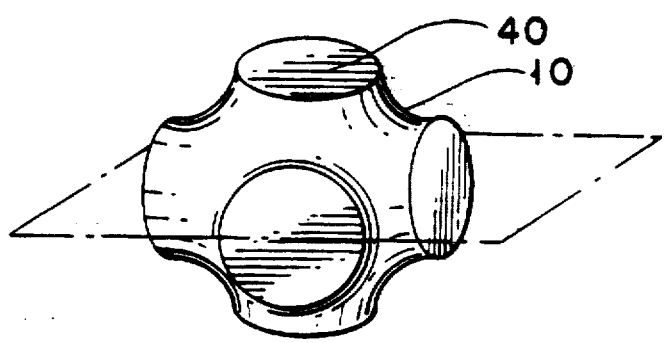
Figure 9C:
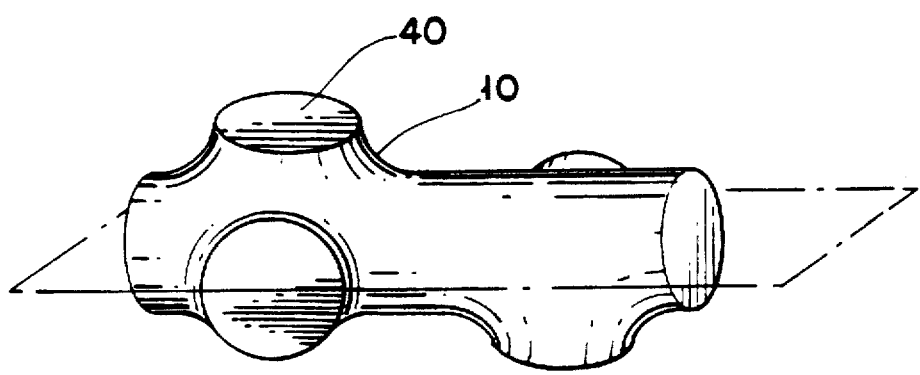

The porous structure depicted in FIG. 8 applies to a unit block of cubic form. This block is shown in isolation in FIG. 9A having cubic protrusions 410 for interconnection with adjacent blocks. For the idealized mathematically minimal surface presented in FIG. 4 and the structure resulting from layering the mesh of FIG. 4 back-to-back in a manner similar to that applied and represented in FIG. 8, the unit block will have the configuration presented in FIG. 9B. Other configurations are possible, consistent with the foregoing features. For example in FIG. 9C, a repeating unit block is depicted, wherein protrusions are offset in two of the three orthogonal planes.

Manufacturing the foregoing mesh structures may be accomplished by select micro-machining techniques. The selection of the appropriate manufacturing technique will be a function of the desired pore diameter, void volume and the selected material. In many medical applications, it is desired to form the porous articles out of a biologically acceptable material, such as silicone rubber. The use of silicone rubber provides some control over the flexibility of the resulting article making it advantageously applied to the artificial blood vessel application. Other polymers may be applied to vary the stiffness and chemical inertness of the resulting structure.

In the following example, a mesh similar to that of FIG. 4 is molded out of silicone rubber. In this process, the first step is to prepare the mold form by creating a mirror image of the desired mesh structure in the form surface. The form is prepared by taking thin sheets of steel, the thickness thereof in the range of the desired mesh thickness. This form is then coated on both sides with a photosensitive film similar to those used in conventional photolithography processes. A mask is prepared having a two-dimensional pattern of openings in a pattern corresponding to the pattern of protrusions for the resulting mesh. The photosensitive material on the top side of the steel form is partially exposed to UV light through the openings of the mask. The steel form is then stripped of the exposed photosensitive material and chemically etched in those locations stripped of the exposed film. The backside of the steel form is treated in a similar manner; thus, resulting in a series of beveled openings extending through the form and a series of protrusions extending from a single surface of the form.

This steel form is then used as a receptacle for the mesh forming polymer. This polymer is applied to the surface in uncured liquid state so that the polymer fills the void spaces of the form. The polymer is then cured forming the semi-rigid mesh structure. The final steps of this process include deflashing the residue of the polymeric material and removing the cured polymeric mesh from the steel form.

The mesh tape provided by the above process may be used directly in the various applications discussed above. To the extent that a porous article having a defined but unusual shape is desired, this unusual shape may be created by the use of a mandrel. In this context, the tape is wrapped around the mandrel forming a helically developed sequence of alternating layers. Adhesives may be used to fix the layers in position. The resulting shape is then removed from the mandrel and applied to its intended use.

The form may also be made by electrical discharge machining (EDM), wherein the specific topographic surface is carved from the steel, via precision guided electrical discharge. More rigid materials will be selected for use where structural stiffness is important. An example of this would be the use of the porous article to rebuild a crushed tibia during reconstructive surgery. For this application, the porous article is made from a fine grain hydroxyapatite ceramic material in the form of the mesh presented in FIG. 4, wherein the dimensions X and Y are approximately 500 microns. A monolithic minimal surface may be formed by sintering an article of alternating plural layers of this mesh at about 1150° C. The resulting article would exhibit significant structural rigidity, a uniform three-dimensional network of interconnecting pores and a void volume approximating 50%. Additional details are available in U.S. Pat. No. 5,348,788, which is incorporated by reference herein.

The above-described arrangement is merely illustrative of the principles of the present invention. Numerous modifications and adaptations thereof will be readily apparent to those skilled in the art without departing from the spirit and scope of the present invention.

What is claimed is:

1. A process for manufacturing a non-woven porous mesh comprising the steps of:

selecting a form having a flat shape and uniform thickness between a first and second side that is suitable for molding polymeric materials;

creating openings in and normal to said form extending therethrough wherein said openings have substantially similar effective diameters and are distributed across the sides of said form in a substantially uniform pattern;

creating plural troughs in the first side of said form whereby a trough, running parallel to the plane of the first side with a width corresponding to the effective diameter of said opening and depth approximately equal to one-half the effective diameter of said openings, is established between each pair of adjacent openings;

filling said form with a curable material in a fluid state;

curing said curable material;

deflashing said cured material; and removing said cured material from said form.

2. The method of claim 1, wherein the steps of creating said openings and troughs further comprises the steps of:

preparing a mask defining the two dimensional location of said openings and troughs;

treating the surface of said form with a photosensitive material;

selectively exposing said form to electromagnetic energy filtered by said mask;

removing the exposed portions of said photosensitive material; and chemically etching the exposed surface of said form.

3. The method of claim 1, wherein the steps of creating said openings and troughs comprises the selective machining of the form using electrical discharge.

4. The method of claim 1, wherein said openings have an effective diameter of 25 to 1000 μm.

* * * * *